United States Patent [19]

Kim

[11] 4,199,411
[45] Apr. 22, 1980

[54] HALIDE ION-SELECTIVE DEVICES AND METHODS OF DETERMINING HALIDES

[75] Inventor: Sang H. Kim, Rochester, N.Y.

[73] Assignee: Eastman Kodak Company, Rochester, N.Y.

[21] Appl. No.: 956,526

[22] Filed: Oct. 31, 1978

[51] Int. Cl.² .................... G01N 27/30; G01N 27/46
[52] U.S. Cl. .................................. 204/1 T; 204/195 P
[58] Field of Search ............... 204/1 B, 195 P, 195 M, 204/195 F

[56] References Cited

U.S. PATENT DOCUMENTS

| | | | |
|---|---|---|---|
| 2,278,248 | 3/1942 | Darrah | 204/195 R |
| 3,305,469 | 2/1967 | Poulos | 204/195 R |
| 3,337,441 | 8/1967 | Goldsmith | 204/195 W |
| 3,493,484 | 2/1970 | Berg et al. | 204/195 R |
| 3,591,482 | 7/1971 | Neff et al. | 204/195 F |
| 3,694,163 | 9/1972 | Sherelis | 195/103.5 R |
| 3,979,274 | 9/1976 | Newman | 204/195 B |

OTHER PUBLICATIONS

R. P. Buck, Proc. Analyt. Div. Chem. Soc., pp. 332-334, Nov. 1977.

*Primary Examiner*—G. L. Kaplan
*Attorney, Agent, or Firm*—Arthur H. Rosenstein

[57] ABSTRACT

Halide, especially chloride and bromide, ion-sensitive devices which are insensitive to uric acid, and other interfering materials while demonstrating extended shelf lives, are described. Such devices comprise a silver halide layer bearing a thin cellulose ester layer which contains at least one polyol having from 2 to 6 hydroxyl groups.

25 Claims, 9 Drawing Figures

HALIDE ION-SELECTIVE DEVICES AND METHODS OF DETERMINING HALIDES

FIELD OF THE INVENTION

The present invention relates to halide ion-sensitive devices and more specifically to halide ion-sensitive electrodes which are insensitive to interference by uric acid and other low molecular weight materials and demonstrate extended shelf lives.

BACKGROUND OF THE INVENTION

Silver/silver chloride (Ag/AgCl) ion-sensitive electrodes comprising a layer of silver in electrochemical contact with a layer of silver chloride are well known in the art, as evidenced by the following U.S. Pat. Nos. 3,883,495; 3,502,560; 3,591,482 and 3,856,649, as well as *Research Disclosure* Publication No. 16113, Volume 161, dated September, 1977.

Such electrodes, in addition to their utility as reference electrodes, are useful for the determination of $Cl^\ominus$ in aqueous solutions. However, they are also extremely sensitive to the presence of uric acid, $Br^\ominus$, and other low molecular weight materials which affect their ability to accurately measure $Cl^\ominus$ activity and, consequently, $Cl^\ominus$ concentration.

Such low molecular weight materials have also been found to interfere with other ion-sensitive electrodes, such as silver/silver bromide electrodes for the measurement of bromide ions where chloride and other ions interfere. To solve this problem, layers or films of polymeric materials, such as cellulose esters, silicone rubber and methyl methacrylate have been provided overlying the electrode. For example, U.S. Pat. No. 3,979,274 describes an enzyme electrode overlaid with a thin layer of one of the foregoing polymeric materials to remove interferences from low molecular weight interferents. U.S. Pat. No. 3,591,482 describes a Ag/AgCl chloride ion-selective electrode bearing a thin layer of methyl methacrylate which serves to protect the electrode from physical damage and corrosion while permitting passage of $Cl^\ominus$. U.S. Pat. No. 3,694,163 describes an enzyme electrode comprising a membrane of a phase inverted cellulose acetate material containing a reagent and an amide swelling agent. The swelling agent is said to, among other things, control response time to steady state.

Although the foregoing solutions to the interference problem described above are apparently satisfactory for some purposes, I have found that they are not entirely satisfactory when a Ag/Ag halide electrode coated with such overlayer which has been stored for some time is used to assay aqueous solutions, especially body fluids and most specifically blood serum, for halide ion content. Furthermore, many of the foregoing proposed solutions to the interference problem involve further problems. For example, testing has indicated that methyl methacrylate overcoats as thin as $7\mu$ for chloride sensitive electrodes provide totally inoperative or radically unstable electrodes. Furthermore, even with cellulose acetate overcoats, the range of useful materials is relatively narrow, i.e., cellulose acetates having an acetyl content below about 36.5 percent tend to dissolve in aqueous solutions, while those having an acetyl content above about 40 percent have too much hydrophobicity to provide desirable relatively short response times.

In copending U.S. application Ser. No. 956,527 entitled "Halide Ion-selective Devices" by Kim, Battaglia and Secord, filed of even data with this application, cellulose acetate overcoats having certain hydrophobic qualities are disclosed as being useful in preventing interference from many low molecular weight materials in halide ion concentration evaluations.

It was discovered, however, that upon aging some change occurs in the overlayer which results in a substantial change in the response time of the electrode (i.e., the time required by the electrode to reach a steady, readable state).

Accordingly, it would be desirable to provide a halide ion-sensitive electrode which possesses the advantages of the electrodes described above and which maintains a rapid response time after aging.

SUMMARY OF THE INVENTION

The present invention provides a halide ion-sensitive device which is substantially free from interference by low molecular weight species, such as $Br^\ominus$, uric acid, etc., and which demonstrates rapid response times even after aging. Such device can be an electrode comprising a layer of silver in electrochemical contact with a layer of silver chloride which in turn bears a halide ion-permeable layer of a cellulose ester containing a polyol having from 2 to about 6 hydroxyl groups. It can also comprise an n- and p-type silicon substrate having thereon a silicon dioxide layer contacted with a silver halide layer containing an overcoat comprising a halide ion-permeable layer of a cellulose ester containing a polyol having from 2 to about 6 hydroxyl groups.

DETAILED DESCRIPTION OF THE INVENTION

Figure 1:
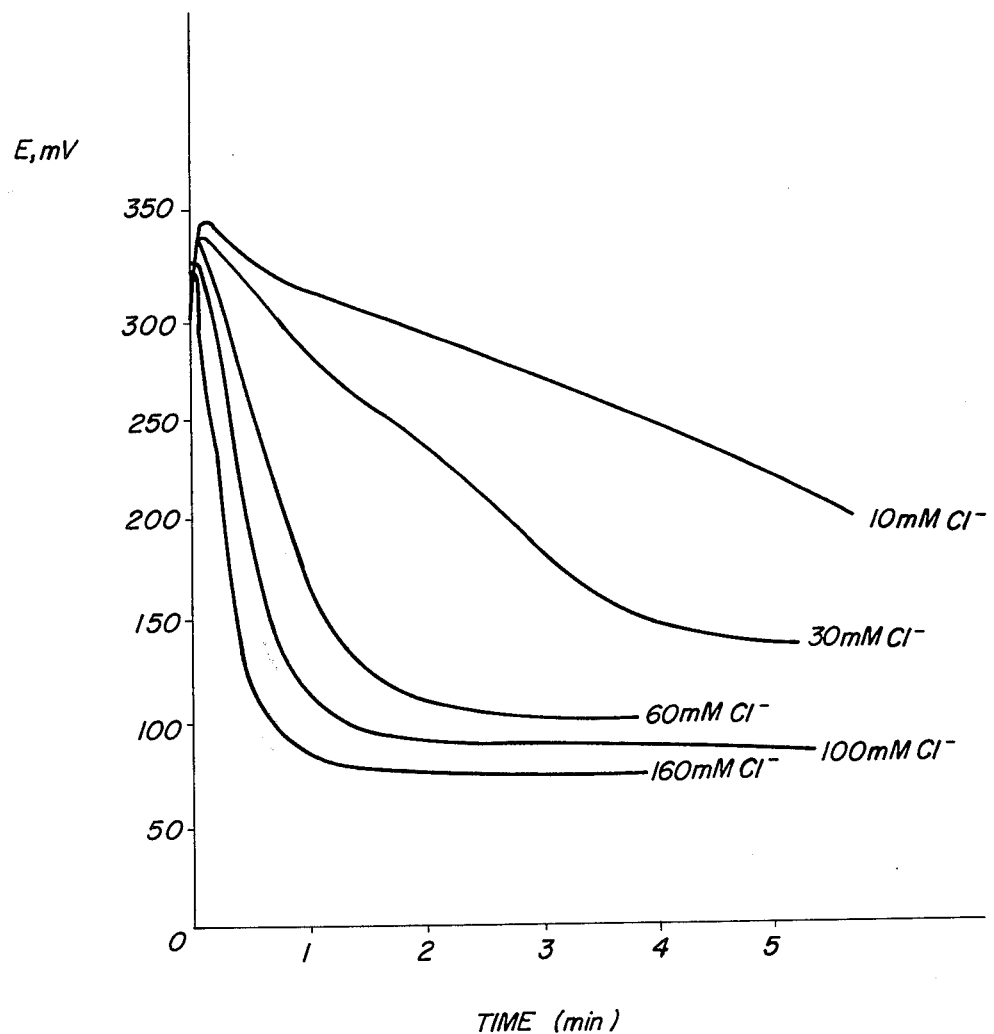
FIGS. 1, 2, 3a, 3b, 4 and 5 are comparison graphs of potential versus time for certain prior art electrodes and those of the present invention.
Figure 2:
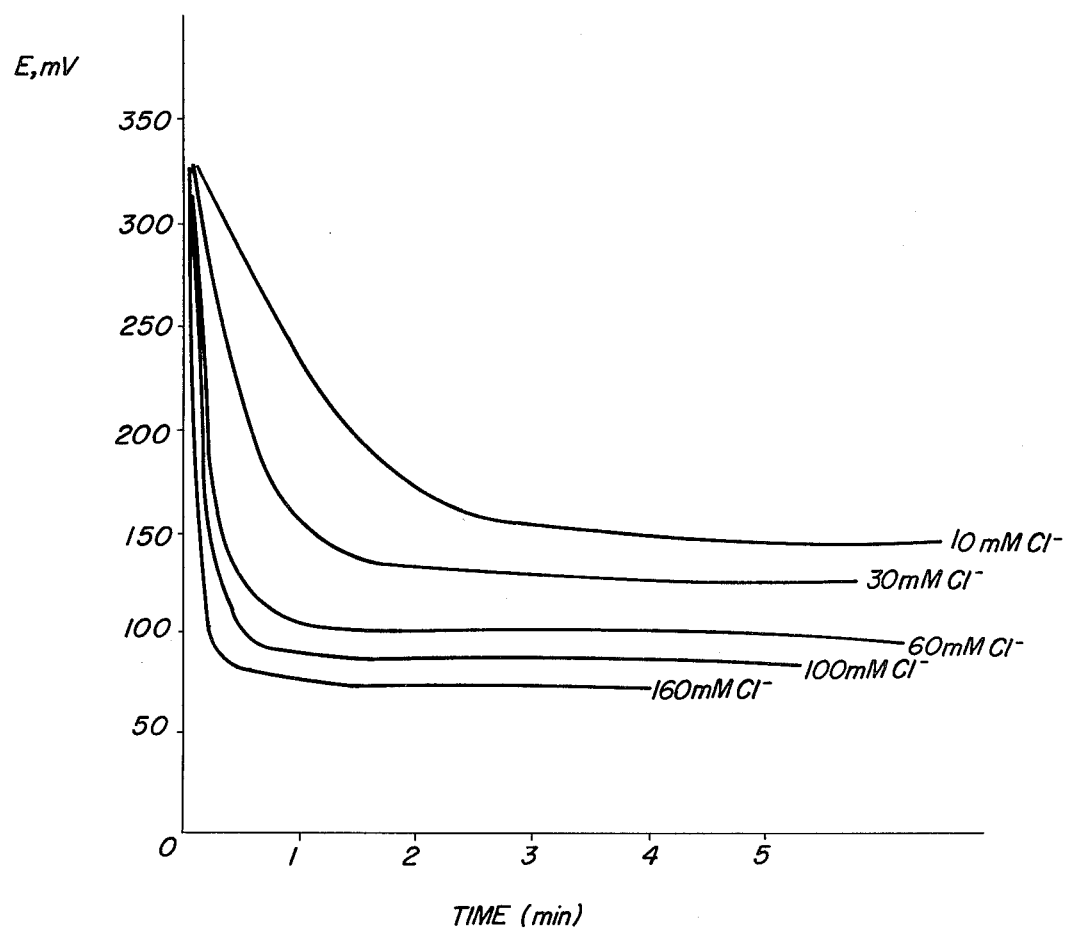

Ag/AgCl electrodes of a variety of formats, compositions and constructions are well known in the art, and their preparation is well documented in numerous patents discussed hereinbelow in the Background of the Invention. Of particular interest are those Ag/AgCl electrodes prepared in the manner and according to the format described in aforementioned *Research Disclosure* Volume 161.

Electrode elements of this type can be prepared using a number of well-known techniques which include, by way of example, dipping a layer of silver such as a wire, foil or supported thin layer of silver into a solution of molten silver halide. According to a preferred embodiment, the silver-silver halide electrode is produced by vacuum-depositing silver onto a suitable support, preferably an insulating polymeric film, and then chemically converting a surface stratum of the silver layer to silver halide. Generally, techniques for chemically converting metal to metal halide involve exposure or contact of the surface of the metal, in this case silver, with a solution of a salt of the halide to be formed for a period and at a temperature sufficient to cause the desired conversion. Typical conditions for this sort of chemical conversion are well known, and examples of simple and preferred techniques may be found in aforementioned *Research Disclosure,* Volume 161. Other useful techniques for preparing such electrodes are described in U.S. Pat. Nos. 3,591,482 to Neff et al, issued July 6, 1971; 3,502,560 to Wise, issued Mar. 24, 1970; and 3,806,439 to Light et al, issued Apr. 23, 1974. Although the teachings of all of these references are directed primarily to the preparation of wire electrodes, the electrodes described herein may also be constructed on thin films of metallized polymeric support, as described in the aforementioned *Research Disclosure,* Volume 161. Alternatively, a discrete layer of silver chloride may be coated over the silver layer so long as appropriate electrochemical contact between the silver and the silver chloride is achieved.

Although it is possible to obtain the silver-silver salt interface with substantially any ratio of silver layer to salt layer thickness, in a preferred embodiment which assures a sufficiently dense layer of silver salt, the salt layer has a thickness equal to at least 10 percent of the overall thickness of the silver layer. According to an especially preferred embodiment, from about 10 to about 20 percent of the thickness of the silver layer is converted to silver chloride using chemical conversion techniques.

The overlayers of the present invention comprise a thin layer of a cellulose ester containing a polyol of from about 2 to about 6 hydroxyl groups.

Among the cellulose esters useful in the overlayers of the present invention are cellulose acetates preferably having an acetyl content of from about 36.5 to about 40 percent, and mixed esters of cellulose, such as cellulose acetate butyrate, cellulose acetate propionate, hydrolyzed cellulose acetate butyrate (preferably having from about 6.4 to about 8.3 percent hydroxyl groups), etc. Generally, however, any cellulose ester which prohibits interference with the potentiometric measurement by low molecular weight materials in a layer is useful as the matrix for the overlayers described herein.

The thickness of the overlayer ranges from about 0.1 to about 20.0$\mu$, and preferably from about 1 to about 8$\mu$, although quite clearly thicknesses outside of this range may be useful for certain applications.

When prepared according to the preferred embodiment hereof, i.e., in a planar format as described in *Research Disclosure,* Volume 161, coverages of from about 1 to about 8 g of cellulose ester per square meter of electrode, depending upon the particular ester, polyol, etc., which is used, are applied to the Ag/AgCl electrode.

Polyols useful in the successful practice of the present invention generally are those having from 2 to about 6 hydroxyl groups. Such materials include diols, triols, polyethylene glycols, alkoxy polyethylene glycols and polypropylene glycols. Among the diols, the preferred materials have chain lengths of from about 4 to about 10 carbon atoms. Examples of useful diols include ethylene glycol, 1,2-propanediol; 1,3-butanediol; 1,5-pentanediol; 2,5-hexanediol; 2-ethyl-1,3-hexanediol; 1,7-heptanediol; 1,8-octanediol; 1,10-decanediol; and 1,14-tetradecanediol. Useful triols include glycerol; 1,3,6-hexanetriol; and 1,2,4-butanetriol. Among the polyethylene glycols, those having molecular weights between about 100 and about 6,000 have been found useful. Most preferred are those having molecular weights of between about 200 and about 600. Alkoxypolyethylene glycols such as methoxy polyethylene glycol are also useful.

Among the polypropylene glycols, those having molecular weights below about 1,100 are specifically preferred. Generally, any polyol of the class described which does not adversely affect the interference-inhibiting characteristics of the cellulose ester layer and extends the shelf life of the electrode as described herein is intended to be within the operative scope of the appended claims. The concentration of polyol which is used will vary broadly depending upon such factors as the ester used to form the layer, layer thickness, etc.; however, polyol concentrations of between about 1 and about 15 percent by weight of the layer have been found most useful and practical and are therefore preferred.

The specific method of application of the overlayer membranes of the present invention is, of course, largely dependent upon the physical shape of the underlying Ag/AgCl or other electrode. Thus, when the Ag/AgCl electrode is a wire electrode, the simplest method for applying the overlayer may be dipping or spraying. When the underlying electrode is in a planar format as described in *Research Disclosure,* Volume 161, referred to above, it is advantageous to coat the overlayer according to techniques well known to those skilled in the coating art, although any technique can be used.

When using a coating mode of application, the cellulose ester layer is generally applied by forming a solution of the polymer in a suitable solvent with the polyol, applying the solution to the electrode, and then driving off the solvent under drying conditions.

Useful solvents include acetone, methyl ethyl ketone, methyl acetate, acetone mixture of methanol, 2-ethoxy ethanol, or diacetone alcohol, and dichloromethane: methanol (90:10 by weight).

Surfactants may also be included in the solutions as appropriate to achieve good coating characteristics. Buffers may also be added if this is appropriate to the solution to be assayed using the electrode.

Figure 8:
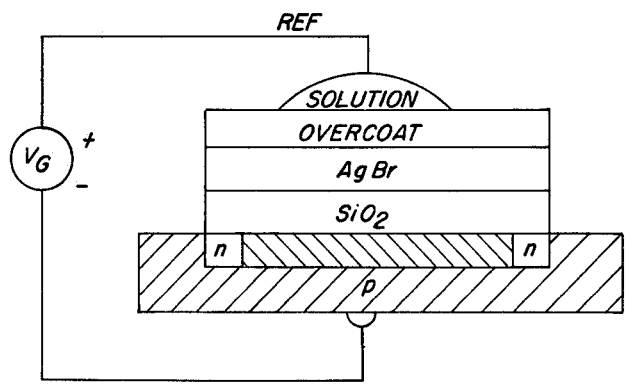
FIG. 8 describes one embodiment of a potentiometric device of the present invention.

A silver halide layer may also be vacuum deposited on a semiconductor substrate, such as silicon dioxide/silicon to prepare a field effect potentiometric sensor. Overlayers of the type described in this application are useful for application to so-called ISFET's, i.e., ion-selective field effect transmitters sensitive to chloride or bromide ion, as described by Bergweld (P. Bergweld, IEEE Trans., Biomed., Eng., 17, 70 [1970], and P. Bergweld, IEEE Trans., Biomed., Eng., 19, 342 [1972]), and R. P. Buck et al, *Analytical Chemistry,* Volume 49, No. 14, December, 1970, page 2315. As illustrated in FIG. 8 of the drawings, such FET's, in the case of bromide- or chloride-selective transistors, can comprise a layer of an insoluble salt, such as silver bromide or silver chloride coated over a silicon dioxide layer to form a gate in contact with a silicon surface appropriately doped to define a p or n channel upon application of a sample under test to the silver halide layer. In such an embodiment, the overcoat layers described herein are coated over the silver halide layer to inhibit the effect of interfering ions which may be present in the sample under assay.

The electrodes of this invention can be used in a "dry-operative" system as described in *Research Disclosure* No. 16113, Volume 161, September, 1977. That is, the support is coated with a silver layer and overcoated with a silver-halide layer and dried and subsequently overcoated with the overcoats of this invention and dried.

The overcoats of this invention have been found to reduce interference in assays for halide ion (particularly chloride and bromide ion) concentrations. Interference from other halides, i.e., bromide from chloride, chloride from bromide; uric acid, and other low molecular weight materials; sulfur- and nitrogen-containing species; and large molecules, such as proteins can be reduced in this manner.

The following examples are presented to better illustrate the successful practice of the invention.

OVERLAYER PREPARATION AND TESTING PROCEDURE

Planar format, dry operative, Ag/AgCl electrodes were prepared by vacuum depositing a layer of silver onto a poly(ethylene terephthalate) support. The surface of this silver layer was converted to AgCl by immersion in a bath of dichromic acid and potassium chloride at a temperature of about 22° C. for a period of 30 seconds.

Cellulose ester was dissolved in a suitable solvent, such as acetone or methylethylketone or the like, at 10 percent by weight. The solution was diluted to about 6 percent and a polyol (1 to 15 percent of cellulose ester) was added. Small amounts of surfactant can also be added as a coating aid. The solutions were then coated at appropriate coating conditions. Unless otherwise stated, the coating conditions were: dew point 28° F. (−2.2° C.), dry bulb temperature 110° F. (43.3° C.) for 8 minutes, 130° F. (54.4° C.) for 4 minutes and 180° F. (82° C.) for 4 minutes.

In an absolute mode, the potential of the electrode was measured by a microreference electrode (MI-401, Microelectronics, Inc.). A 100 $\mu$l drop of Cl$^\ominus$ solution (ionic strength 160 L mM in NaNO$_3$) was spotted onto the electrode, and the potentials (as measured by a Corning Model 110 or 112 pH meter) were recorded as a function of time by both a digital printer (Digitec 6110) and a Hewlett-Packard XY recorder (Model 7045A). The response time of the electrode was chosen as that time at which the potential reached a steady state, i.e., drifted at a constant rate.

In a differential mode, the chloride electrodes were tested using fiber bridges which connect reference and test solutions, as described in *Research Disclosure*, publication 15767, Volume 157, May, 1977. Instruments, similar to those used for absolute measurements, were used to obtain differential measurements.

Stock human serum pools spiked with KBr at 0.5 mM or uric acid or sodium urate at 0.6 mM were used as the abnormally high Br$^\ominus$ and uric acid serum samples, respectively. The differential potential measured by the spiked human serum versus the unspiked human serum ($\Delta$emf) was taken as a measure of the bias in mV (bias expressed as percent equals mV times [−4] assuming the Nernstian slope to be −59 mV/decade).

A three-minute time was chosen as the endpoint. Wherever possible, other potential data at various times were investigated. All tests were performed at ambient conditions (35 to 50 percent RH, 21° to 23° C.), unless otherwise stated.

EXAMPLE 1

Response Times of Cellulose Ester Overcoated Cl$^\ominus$ Electrode with and without Polyols A chloride electrode, made by the process of chemical conversion of Ag°, was overcoated as described above with cellulose acetate (3 g/m$^2$) having an acetyl content of 39.4 percent and a mixture of polydimethyl and polymethylphenylsiloxane (DC-510 from Dow Corning, Midland, Michigan) (0.03 g/m$^2$) as a coating aid. A second electrode was similarly coated, except polyethylene glycol 400 (0.15 g/m$^2$) i.e., 5 percent of cellulose acetate coverage) was added to the cellulose acetate formulation. The coated electrodes were evaluated when fresh as described above using Cl$^\ominus$ concentrations of 10 to 160 mM Cl$^\ominus$ (ionic strength in NaNO$_3$). FIGS. 1 (control) and 2 (electrode of this invention) show the potential time responses of the two electrodes. The electrode containing polyethylene glycol gave a faster response time (earlier leveling off of the slope) than the control and a near-Nernstian slope providing an accurate reading of solutions greater than 30 mM Cl$^\ominus$ at 3 minutes. The electrode without polyethylene glycol did not show a constant slope, even after 5 minutes.

EXAMPLE 2

Comparison of Fresh and Aged Electrodes with and without Polyols

Figures 3A, 3B:
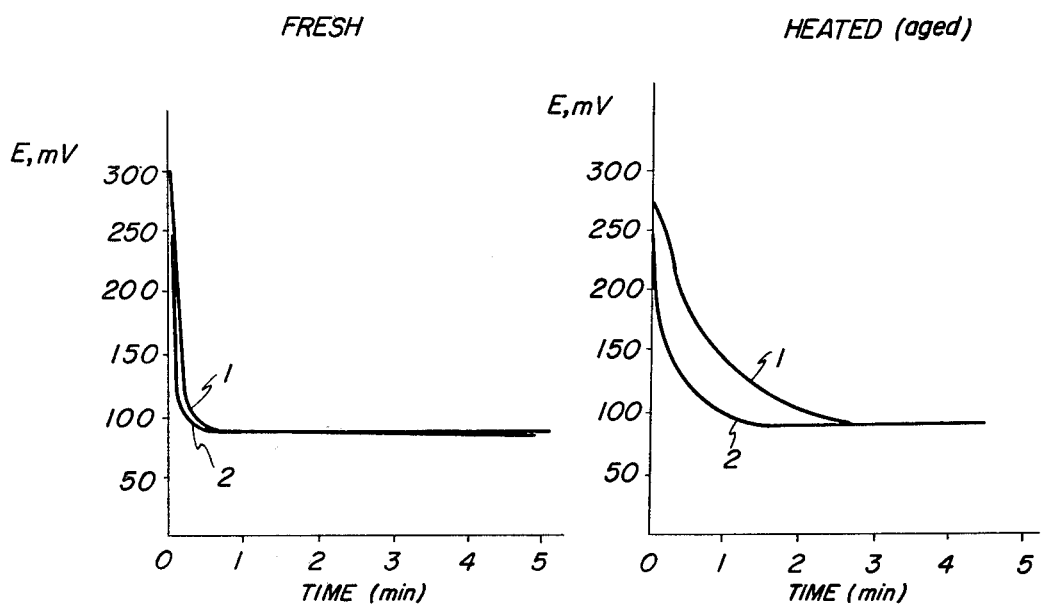

Electrodes as described in Example 1 were tested with 100 $\mu$l drops of 100 mM Cl$^\ominus$ (I equals 160) solutions when fresh and after being heated at 105° C. for 10 minutes. (The heating simulated accelerated incubation or aging). Again, the electrode containing the polyol gave a faster response time when fresh and showed less change in response time upon heating, as shown in FIG. 3 (a and b).

EXAMPLE 3

Stability on Keeping of Cl$^\ominus$ Electrode by the Addition of Polyols

A. The two electrodes described in Example 1 and a third electrode, prepared in a similar manner except containing 2,5-hexanediol (0.15 g/m$^2$), were incubated at various conditions of relative humidity (RH) (15 to 80 percent) and temperature (78° to 120° F.) for 4 weeks. When tested as above, the electrodes without polyols (control) showed response times on the order of:

| 15% RH/78° F. | <50% RH/78° F. | <50% RH/120° F. | <80% RH/78° F. |
|---|---|---|---|
| (2.5 min | <3 min | <5.5 min | <~15 min) |

However, when polyols were added, both 15 and 50 percent RH/78° F. responded at ~1.5 minutes, 50 percent RH/120° F. responded at ~3 minutes, and 80 percent RH/78° F. responded at about 10 minutes. These results indicate that the addition of polyols reduces degradation of the electrodes.

Figure 4:
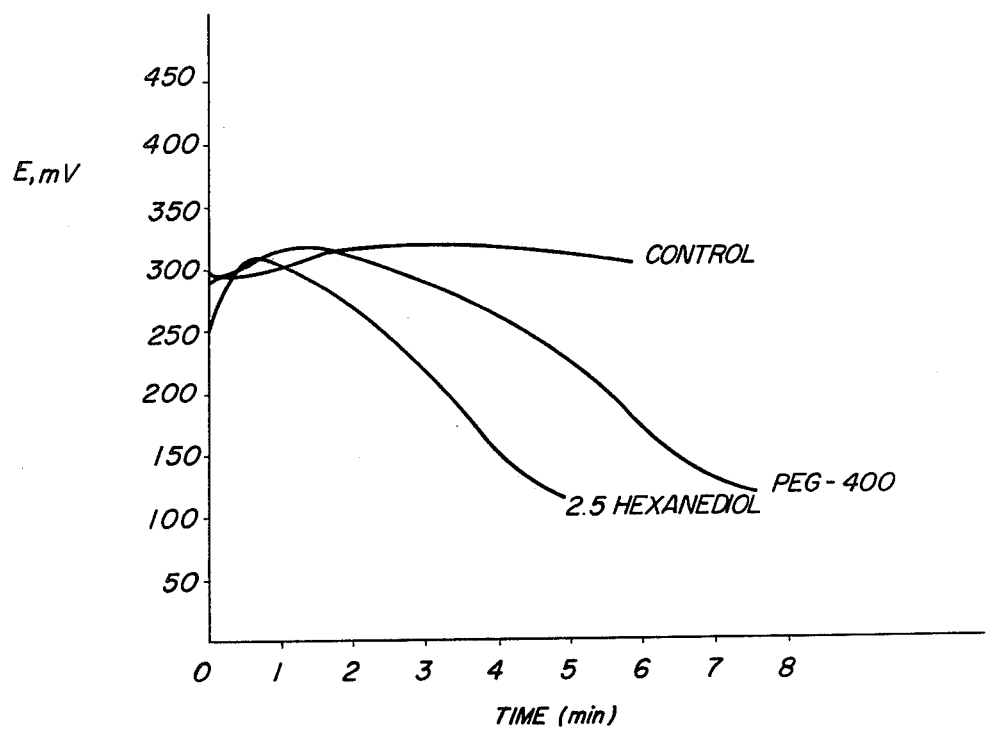
Figure 5:
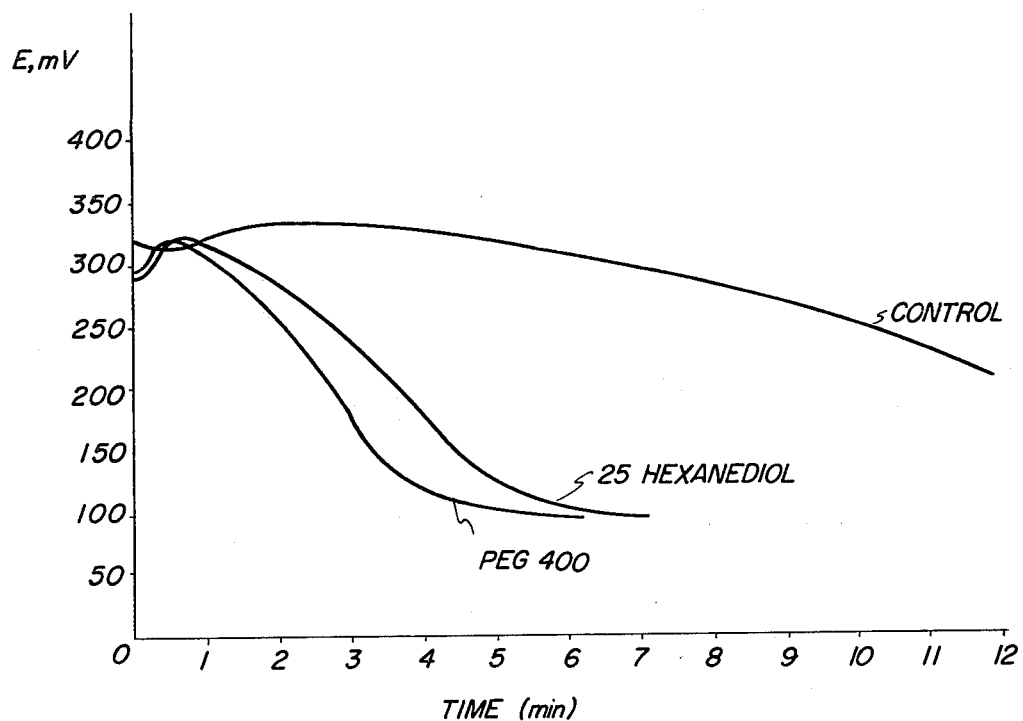

B. The electrodes incubated at 80 percent RH/78° F. were re-equilibrated at ambient conditions for 5 days and then retested as above. Recovery was considerably faster in electrodes which contained the polyols, as shown in FIGS. 4 and 5. The addition of polyols makes the electrode less sensitive to fluctuating conditions of humidity and temperature.

EXAMPLE 4

Effect of Polyols on Interferants such as Br⊖ and Uric Acid, etc.

Low molecular weight materials, such as bromide ions, uric acid, etc., were found to be interferants in serum chloride determinations employing ion-selective electrodes. Errors (biases) as high as 50 percent can occur when interferant levels are high. The sensitivity to these interfering materials was significantly reduced by overcoating the electrode with a thin layer of cellulose ester material prepared as described in copending U.S. application Ser. No. 956,527, referred to herein. The addition of polyols according to this invention to the cellulose formulation did not significantly alter this protection and, in fact, provided greater reproducibility on aged electrodes. Three electrodes, as described in Table I, were tested with Br⊖ and uric acid spiked serum pools, and the bias (percent) obtained from each was calculated.

TABLE I

Bias (percent)

| Electrode | Bromide (0.5 mM) | | Uric Acid (0.6 mM) | |
|---|---|---|---|---|
| | Fresh[a] | 11 Wks Old[b] | Fresh[b] | 11 Wks Old[b,c] |
| Bare | 16 ± 2 | 16 ± 2 | 6 ± 0.4 | 6 ± 0.4 |
| A (3.0 g/m² Cellulose Acetate) | 4 ± 3 | 3 ± 15 | −2 ± 2 | −4 ± 3 |
| B (Cellulose acetate + 0.15 g/m² polyethylene glycol MW 400) | 5 ± 2 | 7 ± 1 | 1 ± 2.5 | 1 ± 0.4 |

[a]Pooled serum control (2 to 3 replicates)
[b]Blood Bank pooled serum (4 replicates)
[c]Duplicate determinations As shown in Table I, reproducibility of the eleven-week old cellulose acetate-coated electrode (A) was very poor compared to the others. As mentioned earlier, this is due to the slow response of the aged cellulose acetate-coated electrode. Table II shows the bias (mV) obtained in four replicate tests made with each of the eleven-week old electrodes using a bromide spiked serum.

TABLE II

| Bias (mV) of 11-Week Old Electrodes (Br⊖ 0.5 mM) | | | | |
|---|---|---|---|---|
| Bare | −3.7 | −4.4 | −4.4 | −3.6 |
| A | 2.4 | −3.9 | 2.6 | −4.0 |
| B | −1.9 | −1.7 | −2.1 | −1.6 |

EXAMPLE 5

Calibration of Five-Week Old Electrodes with and without Polyols

Figure 6:
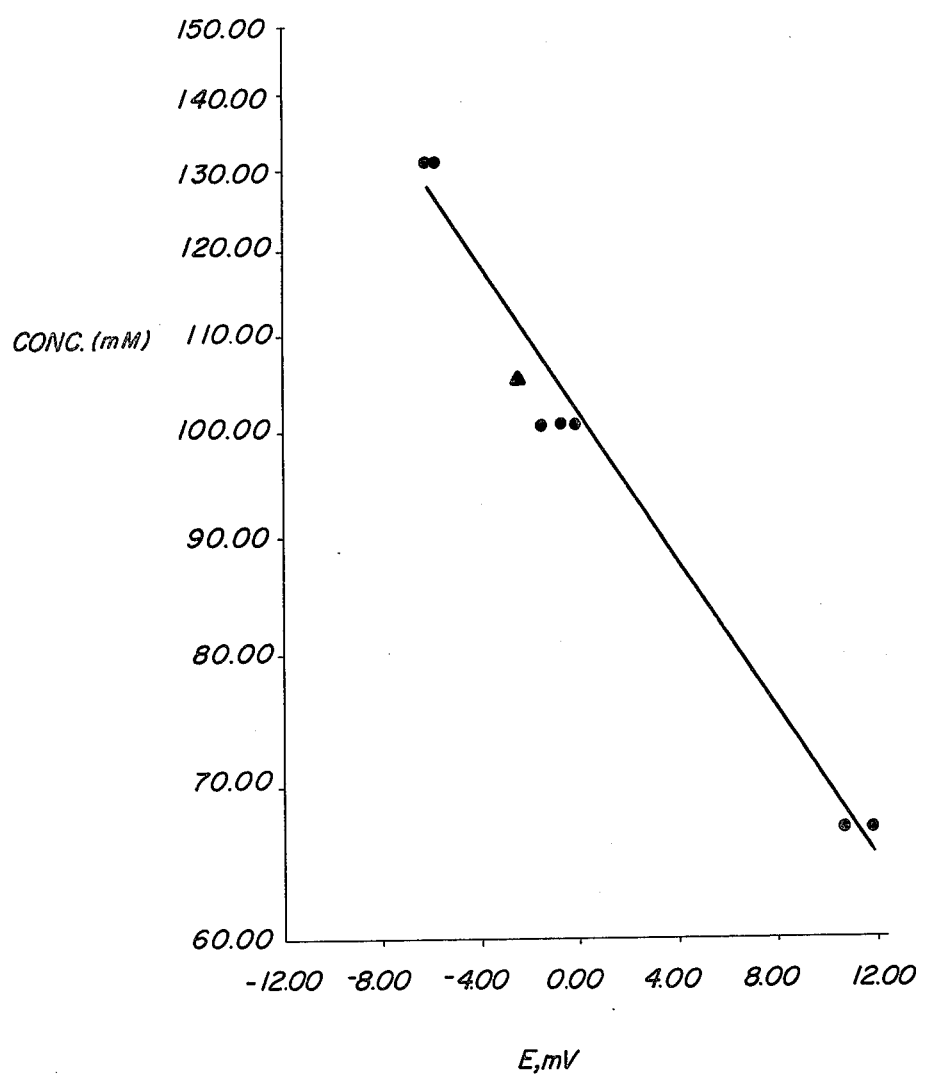
FIGS. 6 and 7 are graphs of concentration versus potential which demonstrate the utility of the electrodes of the present invention.
Figure 7:
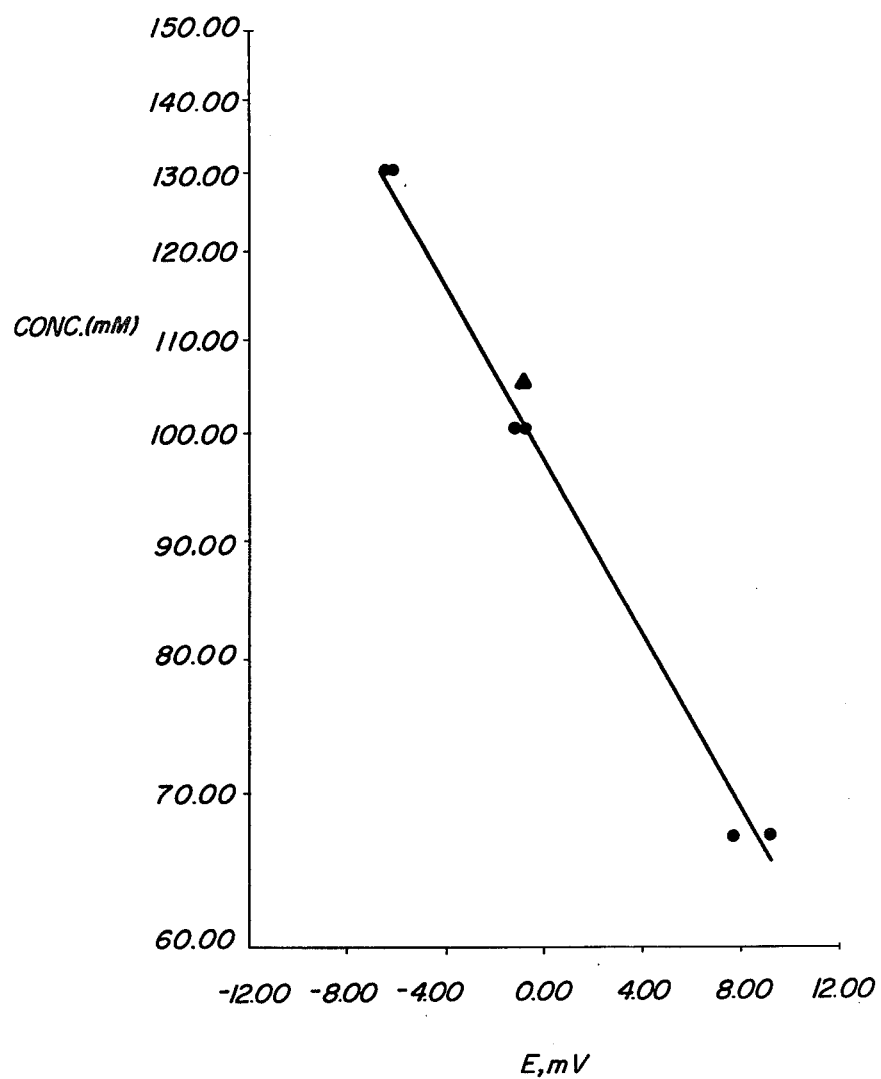

Five electrodes prepared as described in Example 4 were overcoated as shown in Table III. These were kept at ambient conditions (35 to 50 percent RH, 21° to 23° C.) for 5 weeks and subsequently each was calibrated using 3 chloride levels of human serum calibrator. A pooled serum control was assayed, and the bias (mEq/l) was calculated from the calibrated slopes. FIGS. 6 and 7 show the plotted curves of the control electrode and that containing polyethylene glycol (MW 400), respectively. The control coating showed a significant lack of fit in the curve due to the slow response time of the electrode at the lower Cl⊖ concentration.

TABLE III

| | | Calibration and Assay Data | | |
|---|---|---|---|---|
| Electrode | Overcoat Composition | Slope ± Std. Error mV/dec | Pure Error mEq/l | Pooled Serum Control Bias ± Std. Error mEq/l |
| A | Cellulose acetate (3 g/m²) | −61.75 ± 0.05 | 1.95 | 5.98 ± 0.83 |
| B | Cellulose acetate + polyethylene glycol (MW 400) (0.15 g/m²) | −52.80 ± 0.03 | 1.78 | −4.12 ± 3.59 |
| C | Cellulose acetate + 2,5-hexanediol (0.3 g/m²) | −51.76 ± 0.02 | 0.89 | −2.86 ± 0.95 |
| D | Cellulose acetate + 2-ethyl-1,3-hexanediol (0.15 g/m²) | −51.06 ± 0.01 | 1.02 | −3.45 ± 3.41 |
| E | Cellulose acetate + 1,2,6-hexanetriol 0.15 g/m² | −50.87 ± 0.02 | 1.67 | −1.91 ± 1.18 |

The invention has been described in detail with particular reference to preferred embodiments thereof, but it will be understood that variations and modifications can be effected within the spirit and scope of the invention.

What is claimed is:

1. In a potentiometric device for the detection of halide ions in a solution under test, said device comprising a layer of silver halide in electrochemical contact with means for making potentiometric measurements related to halide ion concentration, said layer of silver halide in turn bearing a halide ion permeable overlayer of a cellulose ester which inhibits interference due to low molecular weight materials, the improvement comprising the presence in said cellulose ester overlayer of a polyol containing from 2 to 6 hydroxyl groups which results in an extended useful shelf life of said device.

2. The device of claim 1 wherein said silver halide is silver chloride and said halide ions are chloride ions.

3. The device of claim 1 wherein said means for making potentiometric measurements comprises a doped silicon support having thereon a silicon dioxide layer.

4. The device of claim 1 wherein said cellulose ester is cellulose acetate having an acetyl content of from about 36.5 to 40 percent.

5. In a Ag/Ag halide, halide ion-sensitive electrode comprising a layer of silver in electrochemical contact with a layer of silver halide which in turn bears a halide ion permeable overlayer of a cellulose ester which inhibits interference due to low molecular weight materials, the improvement comprising the presence in said cellulose ester overlayer of a polyol containing from 2 to 6 hydroxyl groups, said overlayer resulting in an extended useful shelf life of said electrode.

6. The electrode of claim 5 wherein the cellulose ester is selected from the group consisting of cellulose acetate, cellulose acetate butyrate and cellulose acetate propionate.

7. The electrode of claim 6 wherein the cellulose ester is cellulose acetate having an acetyl content of from about 36.5 to 40 percent.

8. The electrode of claim 5 wherein the polyol is a diol, triol, polyethylene glycol, alkoxypolyethylene glycol or propylene glycol.

9. The electrode of claim 8 wherein the polyol is selected from the group consisting of diols having chain lengths of from about 4 to about 10 carbon atoms, polyethylene glycols having molecular weights of between about 100 and about 6,000 and polypropylene glycols having molecular weights less than about 1,000.

10. The electrode of claim 5 wherein the polyol is selected from the group consisting of ethylene glycol, 1,2-propanediol, 1,3-butanediol, 1,5-pentanediol, 2,5-hexanediol, 2-ethyl-1,3-hexanediol, 1,7-heptanediol, 1,8-octanediol, 1,10-decanediol, 1,14-tetradecanediol, glycerol, 1,3,6-hexanetriol, methoxy polyethylene glycol and 1,2,4-butanetriol.

11. The electrode of claim 5 wherein said overlayer further includes a surfactant.

12. The electrode of claim 5 wherein said silver halide is silver chloride.

13. A Ag/Ag halide, halide ion-sensitive electrode having an extended shelf life comprising a layer of silver in electrochemical contact with a layer of silver halide which in turn bears a halide ion permeable layer of a cellulose ester containing a polyol having from 2 to 6 hydroxyl groups, said polyol being present in said cellulose ester layer in a concentration sufficient to extend the shelf life of said electrode over the shelf life of said electrode not containing said polyol.

14. A method for determining halide ion concentration in an aqueous solution comprising:
(a) contacting a halide ion permeable overlayer of a potentiometric halide ion-sensitive device with a sample of said solution, said device comprising a layer of silver halide in electrochemical contact with means for making potentiometric measurements related to halide ion concentration, said layer of silver halide in turn bearing a halide ion permeable overlayer of a cellulose ester containing a polyol having from 2 to 6 hydroxyl groups; and
(b) measuring the potential difference between the aqueous solution and the silver halide layer to determine halide ion concentration.

15. The method of claim 14 wherein said halide ion is chloride ion and said silver halide is silver chloride.

16. The method of claim 14 wherein said means for making potentiometric measurements comprises a doped silicon support having thereon a silicon dioxide layer.

17. A method for determining halide ion concentration in an aqueous solution comprising:
(a) contacting a halide ion permeable overlayer of a halide ion-sensitive electrode with a sample of said solution, said electrode comprising a layer of silver which is in electrochemical contact with a layer of silver halide which, in turn, bears as said halide ion-permeable overlayer, a layer of a cellulose ester containing a polyol having from 2 to 6 hydroxyl groups; and
(b) measuring the potential difference between the aqueous solution and the silver layer of the electrode.

18. The method of claim 17 wherein said halide ion is chloride ion and said silver halide is silver chloride.

19. The method of claim 17 wherein the cellulose ester is selected from the group consisting of cellulose acetate, cellulose acetate butyrate and cellulose acetate propionate.

20. The method of claim 19 wherein the cellulose ester is cellulose acetate having an acetyl content of from about 36.5 to 40 percent.

21. The method of claim 17 wherein the polyol is a diol, triol, polyethylene glycol, alkoxypolyethylene glycol or propylene glycol.

22. The method of claim 17 wherein the polyol is selected from the group consisting of ethylene glycol, 1,2-propanediol, 1,3-butanediol, 1,5-pentanediol, 2,5-hexanediol, 2-ethyl-1,3-hexanediol, 1,7-heptanediol, 1,8-octanediol, 1,10-decanediol, 1,14-tetradecanediol, glycerol, 1,3,6-hexanetriol, methoxy polyethylene glycol and 1,2,4-butanetriol.

23. The method of claim 17 wherein said overlayer further includes a surfactant.

24. A method of extending the shelf life of a potentiometric halide ion-sensitive device of the type comprising a layer of silver halide bearing a halide ion permeable overlayer of a cellulose ester, which device is to be used with aqueous solution in electrochemical contact with potentiometric measuring means for determining halide ion concentration, said method comprising incorporating in the cellulose ester overlayer a polyol having from 2 to 6 hydroxyl groups.

25. The method of claim 24 wherein said silver halide is silver chloride.